United States Patent [19]

Iwasa et al.

[11] Patent Number: 4,895,864
[45] Date of Patent: Jan. 23, 1990

[54] ANTIBIOTIC TAN-950A, ITS PRODUCTION AND USE

[75] Inventors: Takashi Iwasa, Kyoto; Shigetoshi Tsubotani; Setsuo Harada, both of Hyogo, all of Japan

[73] Assignee: Takeda Chemical Industries, Ltd., Osaka, Japan

[21] Appl. No.: 184,824

[22] Filed: Apr. 22, 1988

[30] Foreign Application Priority Data

Apr. 30, 1987 [JP]  Japan ................................ 62-107999

[51] Int. Cl.$^4$ .................... A61K 31/42; C07D 261/12; C12P 17/14
[52] U.S. Cl. ................................... 514/380; 548/243; 435/120
[58] Field of Search .......................... 548/243; 514/380

[56] References Cited

U.S. PATENT DOCUMENTS 3,444,187  5/1969  Ueyanagi et al. ................... 548/243
4,256,898  3/1981  Kelly et al. .......................... 548/243
4,504,486  3/1985  Kurkov ................................ 548/243

OTHER PUBLICATIONS

Lambein et al., Chemical Abstracts, vol. 73, No. 126986b, (1970).

Primary Examiner—Mukund J. Shah
Assistant Examiner—E. Bernhardt
Attorney, Agent, or Firm—Wegner & Bretschneider

[57] ABSTRACT

As the novel antibiotic TAN-950A having the structural formula

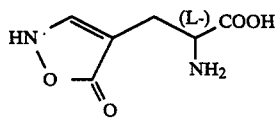

and salt thereof of the present invention show antimicrobial action against fungi, they can be used in the therapeutics of fungal infections, in human and other animals etc. by oral, parenteral or external administration.

2 Claims, 4 Drawing Sheets

ANTIBIOTIC TAN-950A, ITS PRODUCTION AND USE

This invention relates to a novel antibiotic TAN-950A and a salt thereof useful as a anti-fungal agent, a method for producing them, and a microbe capable of producing TAN-950A.

The novel antibiotic TAN-950A of the present invention is a new amino acid type antibiotic in view of its physicochemical and biological data, and such an antifungal antibiotic has never been reported.

Due to the development of therapeutics using chemically synthesized drugs and antibiotics, most of diseases caused by fungi have been overcome. However, most of them have strong toxicity (side effects). Besides long-term or high-dose medication with antibiotics causes changes in the flora of causative agents (microbisme selectionné et substitué) and develops drug-resistance in causative agents. These are counted as important problems in the medical field of the therapy of fungous infections. To solve these problems, in this field, novel antibiotics without toxicity (side effects), or intermediate materials for their synthesis have been sought.

For the purpose of finding out a novel antibiotic the present inventors isolated a great number of microorganisms from soil, from which the antibiotics produced therefrom were separated for study. As the result, the present inventors found that some microbes produce a new antibiotic, that these microbes belong to the genus Streptomyces and that an antibiotic having antifungal activity can be accumulated in a culture medium by incubating said microbes. The present inventors then isolated this antibiotic and, on the basis of its physicochemical and biological properties, the antibiotic was confirmed as a novel antibiotic and named antibiotic TAN-950A.

The present inventors have made, based on these findings, further studies to accomplish this invention.

The present invention relates to:

(1) antibiotic TAN-950A or a salt thereof, (2) a method for producing the antibiotic TAN-950A or a salt thereof, characterized by cultivating a microbe belonging to the genus Streptomyces capable of producing the antibiotic TAN-950A in a culture medium to produce and accumulate the said antibiotic in the cultural broth, then by recovering the same, (3) *Streptomyces platensis* A-136 capable of producing the antibiotic TAN-950A, and (4) a pharmaceutical composition for treating fungal infections, which contains an effective amount of antibiotic TAN-950A or a salt thereof, and a carrier.

In the present specification, "antibiotic TAN-950A" is called simply "TAN-950A" in some cases.

As microbes producing the antibiotic TAN-950A, any microbe can be employed so long as the microbe is capable of producing the antibiotic TAN-950A, while as examples most effectively employable are mentioned a strain which was isolated by the present inventors and named *Streptomyces platensis* A-136 as well as analogous ones thereto. Hereinafter, this strain is simply called strain A-136 in some cases.

Characteristics of the strain are as follows.

This strain forms aerial mycelia on conventional culture media used for classification. These mycelia show monopodial branching, and the spore-bearing hyphae are spiral-shaped. The spore chain consists of more than ten spores. The surface of each spore is smooth, and the size is in the range of 0.8 to 1.2 $\mu m \times 0.9$ to 1.3 $\mu m$. In conventional culture media for classification, no formation of sporangium, flagellate spores or sclerotium is observed.

The growth conditions of this strain on culture media for classification are as follows. Unless otherwise indicated, the descriptions are the results of cultivation at 28° C. for 21 days. The descriptions in parenthesis are color names based on Color Harmony Manual, 4th edition (Container Corporation of America, 1958).

| Cultural characteristics of strain A-136 on various media | | | | |
|---|---|---|---|---|
| Medium | Growth | Color of the surface of colonies | Color of the reverse of the colonies | Diffusible pigment |
| sucrose nitrate agar | moderate spreading | poor pearl(3ba) to pale gray(3dc) | pearl(3ba) | none |
| glucose asparagine agar | moderate restricted | poor, pearl(3ba) | pale yellow(2ca) to yellow(2ea) | none |
| glycerol asparagine agar | good spreading | abundant, white to pale gray(3dc) | pale yellow(2ca) to beige(3ec) | none |
| Inorganic salts starch agar | good | abundant, white to pale gray(3dc) to light brownish gray(3fe), partially black and humid | yellow(2ea) to chamois(2gc) to black | none |
| tyrosine agar | moderate restricted | poor, pearl(3ba) | pearl(3ba) | none |
| nutrient agar | moderate restricted | poor, pearl(3ba) | pearl(3ba) to beige(3ec) | none |
| yeast malt agar | good spreading | abundant, white to bright brownish gray(3fe) to gray (5fe), partially black and humid | pale yellow (2ca) to ocher (2ng) | pale brown |
| oatmeal agar | good diffusing | abundant, pearl (3ba) to bright brownish gray(3fe), partially black and humid | pearl(3ba) to pale yellow(2ca) | none |

Physiological properties of A-136 strain are as follows.

(1) Temperature range for growth: 10° to 36° C., preferably 28° to 32° C.

(2) Liquefaction of gelatin: positive
(3) Hydrolysis of starch: positive
(4) Coagulation and peptonization of skimmed milk: negative
(5) Production of melanoid pigment: negative (peptone yeast iron agar medium)
(6) Reduction of nitrate: negative (International Streptomyces Project No. 8 medium)
(7) Assimilation of carbon sources (Pridham & Gottlieb agar medium):
   Carbon sources well assimilated: inositol, D-mannitol, D-xylose, D-glucose, D-fructose, raffinose,
   Carbon sources fairly assimilated: L-arabinose
   Carbon sources not assimilated: rhamnose, sucrose IN HCl-hydrolyzate of the mycelia of A-136 strain was detected LL-diaminopimelic acid, from which this strain is considered to belong to the genus Streptomyces. As the result of comparing the morphological characteristics, observation on culture media and physiological properties of A-136 strain with those of known species, this strain has been identified as *Streptomyces platensis* and named *Streptomyces platensis* A-136.

*Streptomyces plastensis* A-136 employed in the present invention has been deposited under the accession number of IFO 14603 at the Institute for Fermentation, Osaka (IFO) since Apr. 22, 1987. Also this microorganism was deposited at Fermentation Research Institute, Agency of Industrial Science and Technology, Ministry of International Trade and Industry (FRI) under the accession number of FERM P-9358 on Apr. 30, 1987, the deposit being converted to a deposit under the Budapest Treaty, and stored at FRI under the accession number of FERM BP-1786.

In the invention, the known strains *Streptomyces hygroscopicus* A-300 (FERM P-1312), *Streptomyces hygroscopicus* subsp. *augustmyceticus* IFO 3934 and IFO 3935 and *Streptomyces hygroscopicus* subsp. *hygroscopicus* IFO 14102 can also be used.

As their common traits, microorganisms belonging to the genus Streptomyces are ready to change some microbiological properties, and *Streptomyces platensis* A-136 is not an exception. Therefore, the properties of this strain are not definitive as mentioned above, and various mutants of this strain can be easily obtained. However, these mutants can also be employed in the method of this invention, so long as they do not lose the capability of producing the antibiotic TAN-950A. It does not matter, of course, whether such mutation has taken place spontaneously or been artificially induced by using various mutagens (e.g. ultraviolet ray, X-ray, radioactive rays, nitrosoguanidine, etc.).

In the method of this invention, culturing is carried out using a medium containing carbon sources generally assimilable by microorganisms, digestible nitrogen sources, inorganic salts and so on. In the medium, there may be incorporated, as required, trace nutrients, growth promoters, precursors, etc. The generally assimilable carbon sources include glucose, sucrose, molasses, starch, dextrin, glycerin, etc. and the digestible nitrogen sources include meat extract, soybean meal, corn steep liquor, peptone, casein, cotton seed meal, etc. as well as inorganic nitrogen compounds such as nitrates, ammonium compounds, etc. These materials can all be employed to advantage. While surface cultivation is feasible, aerobic submerged culture is more generally useful. In carrying out aerobic submerged culture, the pH of medium is preferably near neutral and the incubation temperature is maintained around 20° C. to 36° C., preferably 24° C. to 30° C. These culture conditions such as the composition and pH of medium, incubation temperature, severity of agitation, etc. may of course be controlled and selected so that they will provide satisfactory results, according to the particular strain of microorganism used, external conditions and other factors.

For harvesting the objective TAN-950A from cultures, separation methods which are usually employed to isolate metabolites produced by microbes from their cultures can be properly used. For example, TAN-950A, which is a water-soluble amphoteric substance, is contained mainly in culture filtrate, and it is recovered advantageously by the following procedures. That is, the whole culture broth, after addition of a filter aid, is subjected to filtration or centrifugation to remove cells, and the resulting culture filtrate is put in contact with a proper carrier to adsorb the active components in the filtrate, and the active components are then desorbed using an appropriate solvent to separate and recover the purposed products. Chromatographic carriers which can be used favorably include compounds with which adsorbability difference is applied, such as activated charcoal, powdered cellulose and adsorptive resins, those with which functional group difference is applied, such as ion-exchange resin, ion-exchange cellulose and ion-exchange cephadex, and those with which a molecular weight difference is applied, such as molecular sieve carriers. Eluents which can be used in proper combination to elute objective compounds from these carriers include hydrous solutions of water-soluble organic solvents, such as hydrous acetone and hydrous alcohols, and aqueous solutions containing acids, alkalis, buffer solutions, inorganic salts or organic salts, though combination varies with types and properties of the carriers.

To describe in more detail, use is made of, as the carrier, for example, cation exchange resin such as Amberlite IR-120 (Rohm & Hass Co., USA), Dowex 50W (Dow Chemical Co., USA) or Diaion SK1A (Mitsubishi Chemical Industries, Ltd., Japan) or anion exchange resin such as Amberlite IRA-402, IRA-68 (Rohm & Haas Co., USA), Dowex 1 (Dow Chemical Co., USA), Diaion SA10B, PA-404, WA-30 (Mitsubishi Chemical Industries, Ltd., Japan), etc. to adsorb the present antibiotic in the filtrate, then the thus-adsorbed materials are eluted with an acid, alkali or aqueous solution containing an acid or a buffer solution. The present antibiotic can also be allowed to be adsorbed on a carrier, for example, ion exchange molecular sieve type resin such as QAE or CM-sephadex (Pharmacia, Sweden), and then the thus-adsorbed materials are eluted with an aqueous solution or buffer solution containing a salt, alkali or an acid. For removing salts, coloring substances, etc. from the resulting eluates, use is made of, with advantage, activated charcoal for chromatography (Takeda Chemical Industries, Ltd., Japan), adsorptive resins such as Diaion HP-20 and SP-207 (Mitsubishi Chemical Industries, Ltd., Japan), Amberlite XAD-II (Rohm & Haas Co., USA), molecular sieve type resin Sephadex (Pharmacia, Sweden) or crystalline cellulose (Asahi Chemical Industry Co., Ltd.), etc. To remove fat-soluble substance or the like in the filtrate or the eluate, a suitable combination of procedures of allowing the eluate to pass through the filtrate or the eluate, or treating the filtrate or the eluate with a water-immiscible organic solvent such as dichloromethane, ethyl acetate, methyl isobutylketone, etc. is employed.

For complete purification of the compound, the high performance liquid chromatography (HPLC) is used with advantage. Carriers which can be used in such HPLC include reverse phase type resin such as YMC gel (Yamamura Chemical Laboratories, Japan) or TSK gel (Toyo Soda Manufacturing Co., Japan). As the mobile phase, use is made of a solvent system prepared by adding an ion paired reagent such as tetrabutylammonium hydride to a buffer solution, etc.

The eluate fraction thus purified and fractionated above can be subjected to concentration, freeze-drying or crystallization to pulverize or crystallize TAN-950A.

TAN-950A was isolated as the monosodium salt, but the free TAN-950A can be prepared by the following procedure. Namely, the TAN-950A monosodium salt is dissolved in water, to which was added one equivalent of hydrochloric acid, and the mixture is subjected to a crystalline cellulose column chromatography, followed by elution with a hydrous alcohol such as methanol-water, propanol-water, etc. to thereby obtain TAN-950A (free form). And the solution containing the antibiotic may be subjected to a column chromatography using Amberlite IR-120 ($H^+$ type), followed by elution with aqueous ammonia to obtain TAN-950A. For preparing pharmacologically acceptable salts (e.g. potassium salt, calcium salt, etc.) from TAN-950A (free form), per se conventional methods are employed.

The culture filtrate was processed with ethyl acetate, and the aqueous layer was subjected to a TLC-bioautography using Candida albicans [carrier: cellulose f, Tokyo Kasei, Co., solvent system: acetonitrile:water (3:1)] to detect two inhibition zones, one of them being in agreement with that of TAN-950A [Rf=0.16 (A)] and the other showing Rf=0.44 [tentatively referred to TAN-950B]. The spot of A was detected at 254 nm of UV lamp, while detection of the spot of B was impossible. On the other hand, the eluate of IR-120B chromatography was subjected to HPLC [carrier: YMC-Pack AM 324 (Yamamura Chemical Laboratories, Japan, mobile phase: 0.005M tetrabutylammonium hydride/0.02M phosphate buffer (pH 6.0), flow rate: 2 ml/minute)]. Two peaks were mainly observed with a detector of 214 nm, one of them being in agreement with that of TAN-950A (Rt=4.8 minutes), while the other showing Rt=5.0 minutes. The eluate fraction of this HPLC was subjected to a TLC-bioautography similar to that in the case of the filtrate to find that the peak eluate fraction of Rt=4.8 was in agreement with the Rf value of A and the peak fraction of Rt=5.0 was in agreement with that of B. The purified TAN-950A was dissolved in a 0.05M phosphate buffer solution (pH 7.0) (1 mg/ml), and the solution was heated at 60° C. Variation with time was examined by the height of peaks of HPLC to find that, after 30 minutes, TAN-950A decreased by 25% while B increased by 20% and, after 2 hours, A decreased by 34% while B increased by 28%. For isolating TAN-950B, fractions containing A and B in a substantially the same amount in the eluate of QAE-sephadex A-25 column chromatography (refer to Example 2 described later) were combined and concentrated. In the concentrate, no substantial amount of B was detected, while the increase of A approximately proportional to the decrease of B was observed. From the facts described in the foregoing, existence of the antifungal substance TAN-950B readily interchangeable with TAN-950A in the filtrate was suggested.

And, TAN-950A contains amino group, and this functional group can be acylated. The N-acylation is carried out by a per se known method. For example, in the case of benzoylation, TAN-950A is dissolved in an alkaline aqueous solution such as a 2% solution of sodium hydrogencarbonate, which is then allowed to react with 2 to 3 mol. of benzoyl chloride.

The physico-chemical properties of TAN-950A (monosodium salt) obtained in Example 2 described later are as follows.

(1) Appearance: white solid
(2) Specific rotation: $[\alpha]_D^{23} -70°\pm10°$ (c=0.524, in water)
(3) Elemental analysis (%):

|  | C | H | N | O | Na |
|---|---|---|---|---|---|
| Found | 33.64 | 4.31 | 12.72 |  | 11.0 |
| Calcd.* | 33.97 | 4.28 | 13.21 | 37.82 | 10.66 |

Figure 1:
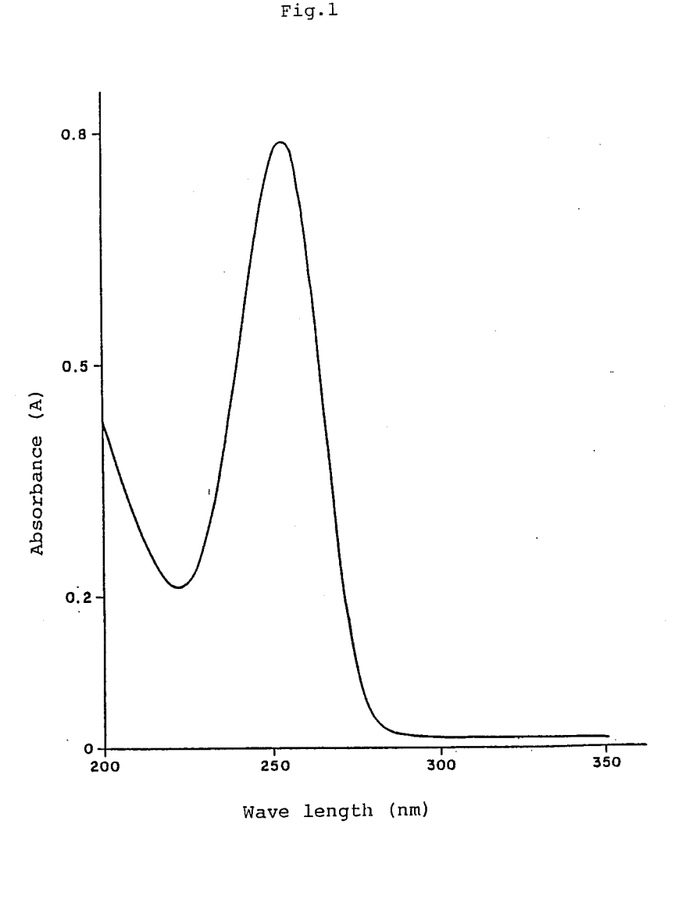
FIG. 1 shows ultraviolet absorption spectrum (in water)
Figure 2:
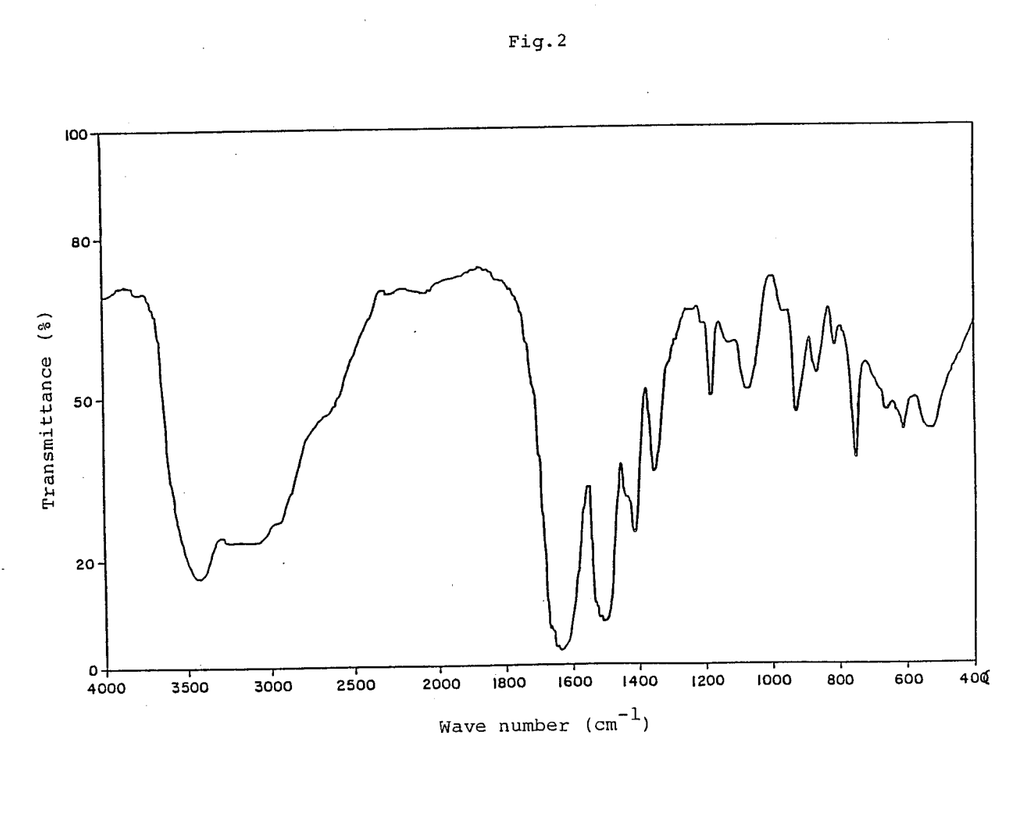
FIG. 2 shows infrared absorption spectrum (KBr method)
Figure 3:
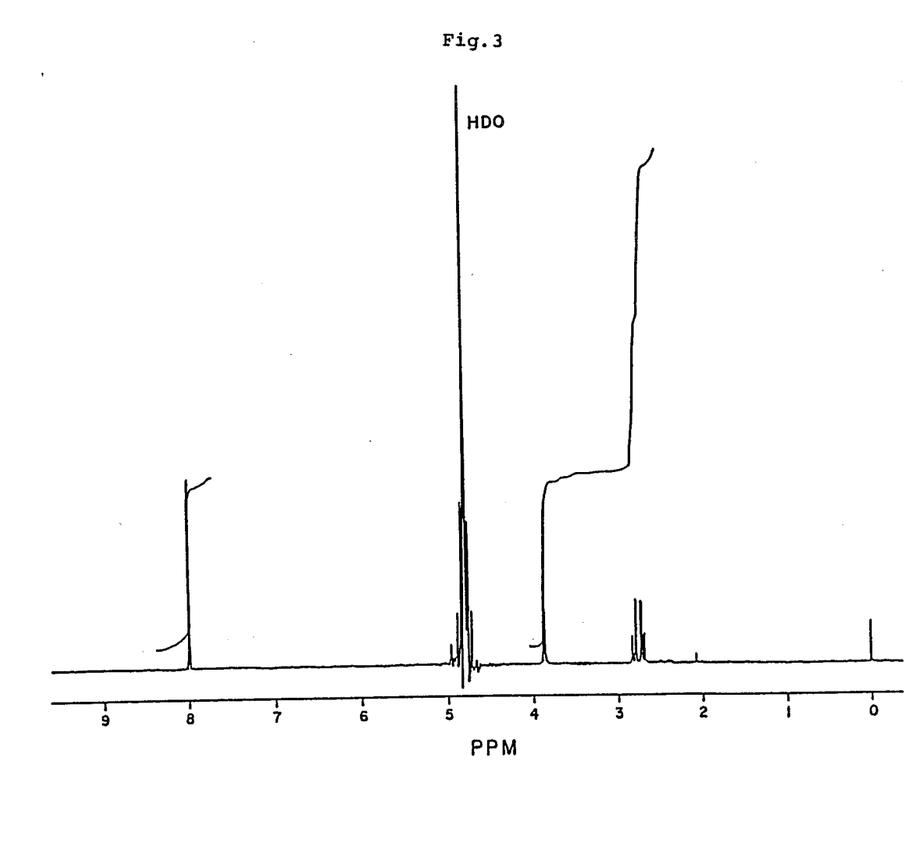
FIG. 3 shows $^1$H nuclear magnetic resonance spectrum (400 MHz, in deuterium oxide)
Figure 4:
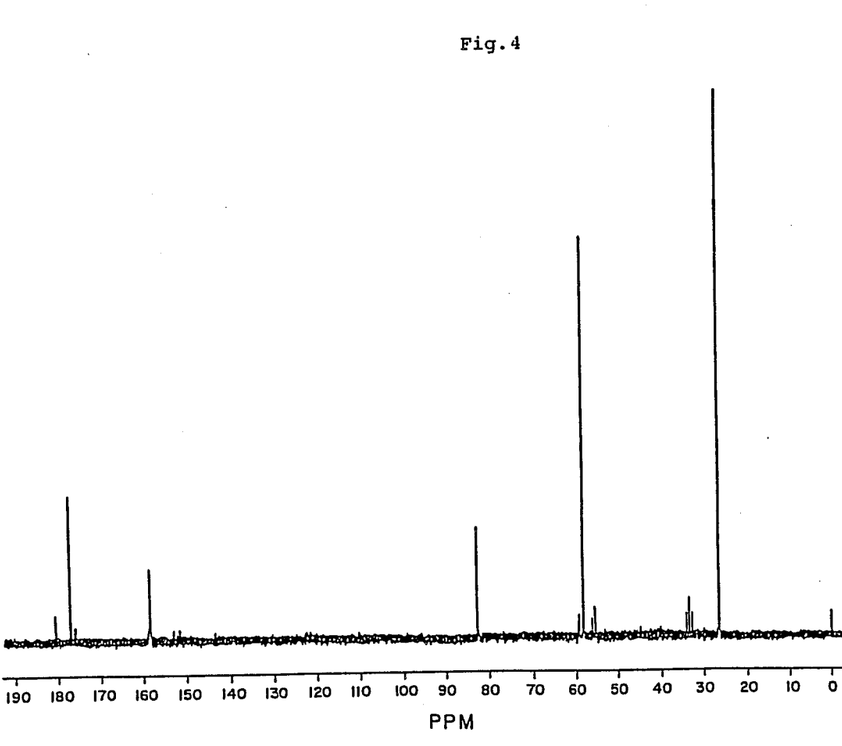
FIG. 4 shows $^{13}$C nuclear magnetic resonance spectrum (100 MHz, in deuterium oxide) of the antibiotic TAN-950A (monosodium salt) obtained in Example 2, respectively.

(*calculated as containing 1 mole of water):

(4) Molecular weight (SI-MS method) m/z 195 $(M+H)^+$, 217 $(M+Na)^+$, 239 $(M+2Na)^+$
(5) Molecular formula: $C_6H_7N_2O_4Na$
(6) UV spectrum: in water (cf. FIG. 1)
$\lambda_{max}$ 353±3 nm ($E_{1\ cm}^{1\%}$=380±50) (in water)
$\lambda_{max}$ 259±3 nm ($E_{1\ cm}^{1\%}$=421±50) (in N/10HCl)
$\lambda_{max}$ 255±3 nm ($E_{1\ cm}^{1\%}$=373±50) (in N/10NaOH)
(7) IR spectrum: in KBr tablet (cf. FIG. 2) Main absorption wavenumbers ($cm^{-1}$) are as follows: 3430, 1640, 1500, 1410, 1350, 1180, 1070, 930, 870, 810, 750, 610, 530
(8) $^1$H-NMR spectrum: 400 MHz, in deuterium oxide (cf. FIG. 3) The following signals are measured ($\delta_{ppm}$ $J_{(Hz)}$). 2.70 (1H, dd, J=7.3, 15.6), 2.80 (1H, dd, J=4.4, 15.6), 3.86 (1H, dd, J=4.4, 7.3), 7.98 (1H, s) (dd: double doublet, s: singlet)
(9) $^{13}$C-NMR spectrum: 100 MHz, in deuterium oxide (cf. FIG. 4) The following signals are measured ($\delta_{ppm}$) 180.6 (s), 177.1 (s), 158.5 (d), 82.9 (s), 58.5 (d), 26.5 (t) (s: singlet, d: doublet, t: triplet)
(10) Solubility:
Soluble: water, dimethyl sulfoxide, methanol
Sparingly soluble: ethyl acetate, acetone, chloroform
(11) Color reaction:
Positive: ninhydrin, Ehrlich (acid), phosphorus molybdate, dimethylaminobenzaldehyde reaction
Negative: Greig-Leabacks's, Dragendorff's reactions
(12) Thin-layer chromatography (TLC):

| Carrier | Solvent system | Rf |
|---|---|---|
| cellulose f*1 | acetonitrile:water (4:1) | 0.11 |
| silica gel GF254*2 | n-butanol:acetic acid:water (2:1:1) | 0.17 |

*1Tokyo Kasei Co., Japan
*2E. Merck AG., W. Germany (13) High Performance Liquid Chromatography (HPLC):
Carrier: YMC-Pack AM-324, manufactured by Yamamura Chemical Laboratories
Mobile phase: 0.005M tetrabutylammonium hydride/0.02M phosphate buffer solution (pH 6.0)
Flow rate: 2 ml/min. Rt=4.8 (min.)
(14) Classification of substance: amphoteric substance
(15) Amino acid analysis: TAN-950A was heated at 110° C. in 6N HCl for 16 hours, followed by subjecting to amino acid analysis to detect glutamic acid.

From the physico-chemical properties of TAN-950A and N-benzoyl TAN-950A obtained in Example 4 and further the X-ray analysis data of N-benzoyl TAN-950A, the structure of TAN-950A was determined as follows:

TAN-950A

The biological characteristics of TAN-950A are described as follows.

Paper discs (8 mm. in diameter, manufactured by Toyo Seisakusho) immersed in an aqueous solution of the antibiotic TAN-950A (monosodium salt) (1000 μg/ml) were put on agar plates seeded with the test organism, and these agar plates were incubated at a given concentration for a given period of time. The length of diameters of the growth inhibition zone formed around the discs was shown in Table 1. In the Table, "0" means no formation of the growth-inhibition zone. Culture media employed are as follows:

A: Sabouraud's dextrose agar medium
B: Yeast nitrogen base agar medium (Difco Laboratories, USA) supplemented with L-asparagine (0.17%)
C: Trypticase soy agar (Becton Dickinson Co., USA)
D: Yeast nitrogen base agar medium (Difco Laboratories, USA) supplemented with glucose (2%) and agar (1.5%)

TABLE 1

Antimicrobial Spectrum of Antibiotic TAN-950A

| Test organism | Medium | Temp. (°C.) | Time (h) | Diameter of growth-inhibition zone (mm) |
| --- | --- | --- | --- | --- |
| Candida albicans IFO 0583 | B | 28 | 48 | 21 |
| | D | 28 | 48 | 34 |
| Candida utilis IFO 0619 | B | 28 | 48 | 0 |
| | D | 28 | 48 | 0 |
| Candida parakrusei IFO0640 | D | 28 | 48 | 43 |
| Candida parapsilosis IFO1396 | D | 28 | 48 | 40 |
| Candida tropicalis IFO0006 | D | 28 | 48 | 25 |
| Torulopsis glabrata | B | 28 | 48 | 23 |
| IFO 1085 | D | 28 | 48 | 26 |
| Filobasidium uniguttulatum | B | 28 | 48 | 23 |
| IFO 0699 | D | 28 | 48 | 35 |
| Cryptococcus neoformans | B | 28 | 48 | 0 |
| IFO 0410 | D | 28 | 48 | 27 |
| Saccharomyces cerevisiae | B | 28 | 48 | 24 |
| IFO 0209 | D | 28 | 48 | 25 |
| Aspergillus fumigatus | B | 28 | 48 | 0 |
| IFO 6344 | D | 28 | 48 | 57 |
| Trichophyton rubrum | A | 28 | 48 | 0 |
| IFO 5467 | D | 28 | 72 | 47 |
| Microsporum gypseum | D | 28 | 72 | 41 |
| IFO 6075 | | | | |
| Penicillium chrysogenum | B | 28 | 66 | 0 |
| IFO 4626 | D | 28 | 72 | 35 |
| Bacillus subtilis PCI 219 | C | 37 | 20 | 0 |
| Escherichia coli NIH JC-2 | C | 37 | 20 | 0 |

As shown in Table 1, the antibiotic TAN-950A shows an antimicrobial activity against certain species of fungi.

Table 2 shows the therapeutic effects of TAN-950A monosodium salt to experimental candidosis in mice.

TABLE 2

| Microbes infected[1] | Route of Administration[2] | $ED_{50}$ (mg/kg)[3] |
| --- | --- | --- |
| Candida albicans | Subcutaneous | 40 |
| Candida albicans | Oral | 105 |

[1] intravenously infected,
[2] twice administration
[3] total of dosages.

No acute toxicity of TAN-950A (monosodium salt) in mice was observed by intravenous, subdermal, intraperitoneal or oral administration in a dose of 4000 mg/kg.

As clearly shown in these data, TAN-950A shows antimicrobial activity against fungi while showing no toxicity to, mammals. Therefore, TAN-950A can be used in the therapeutics for fungal infections in humans, domestic animals, domestic fowls, etc.

For this therapeutic use, TAN-950A can be prepared into medicinal compositions of various forms in accordance with known formulation techniques.

For common use of TAN-950A in the therapeutics of candidiasis, for example TAN-950A can be administered as injections non-orally, intravenously, subcutaneously or intramuscularly, by dissolving in physiological saline, usually at a dose of 1 to 50 mg/kg/day, preferably 5 to 20 mg/kg/day. And, when the antibiotic TAN-950A is given orally, it is prepared into capsules by mixing with lactose or into sugarcoated tablets by conventional processes and administered at a dose of usually 1 to 100 mg/kg/day, preferably 5 to 50 mg/kg/day.

And, TAN-950A obtained by the present invention can also be used as a disinfectant for topical use. For example, TAN-950A can be used for sterilization and disinfection of skin or mucous membrane of humans and animals by applying it as a liquid composition prepared by dissolving TAN-950A in, for example, distilled water at a concentration of usually 0.1 to 10 W/V%, preferably 0.5 to 5 W/V% or an ointment containing, using vaseline or lanolin as a base, usually 0.2 to 100 mg, preferably 1 to 20 mg of TAN-950A per gram.

The antibiotic TAN-950A is a promising compound as an intermediate for the synthesis of novel medicinal products.

The following examples describe the present invention in more detail, but are not intended to limit the invention thereto. Unless otherwise specified, % means weight/volume %. The HPLC conditions are the same with those mentioned before.

EXAMPLE 1

Five hundred ml of a medium (pH 7) composed of 2.0% glucose 3.0% soluble starch, 1.0% corn steep liquor, 1.0% soybean meal, 0.5% peptone, 0.3% sodium chloride and 0.5% calcium carbonate in a 3 l-Sakaguchi flask was sterilized and inoculated with one loopful of A-136 (IFO 14603, FERM BP-1786) grown on a slant culture medium, which was subjected to reciprocal shaking culture at 28° C. for 48 hours. The entire quantity (500 ml) of the resulting culture broth in the Sakaguchi flask was added to 30 l of the medium prepared by adding 0.05% Actocol (manufactured by Takeda Chemical Industries, Ltd., Japan), an antifoaming agent, to the above-mentioned medium in a 50 l stainless steel tank. Submerged cultivation was carried out at 28° C. under aeration of 30 l/min. and agitation at 280 rpm for 48 hours to obtain a seed culture broth.

Six l of said seed culture broth was added to 120 l of a medium (pH 7.0) composed of 0.5% glucose, 5% dextrin, 3.5% soybean meal and 0.7% calcium carbonate in a 200 l of a stainless steel tank. Cultivation was carried out at 28° C. under aeration of 120 l/min. and agitation at 200 rpm for 90 hours.

EXAMPLE 2

The culture broth (100 l) obtained in Example 1, after being adjusted to pH 8.0, as subjected to filtration by the aid of Hyflo Super-Cel (Johnes Manville, USA) to obtain a filtrate (85 l). The filtrate was adjusted to pH 3, to which was added ethyl acetate (40 l), and the mixture was stirred, followed by removal of the ethyl acetate layer. The aqueous layer thus obtained was concentrated, and the concentrate (50 l) was adjusted to pH 5, which was then subjected to a column chromatography on Amberlite IR-120 (H$^+$ type, 8 l). The antibiotic was eluted with a 2% aqueous ammonia, and the eluate (40 l) was concentrated. The concentrate (18 l) was allowed to pass through a column packed with Diaion HP-20 (8 l), and the column was washed with water (12 l). The effluence and the washing were combined and concentrated. The concentrate (3.3 l) was subjected to a column chromatography on Diaion SP-207 (2 l). Elution was carried out with water for fractionation. Fractions containing the antibiotic were combined (5 l), which was subjected to a column chromatography on QAE-sephadex A-25 (Cl$^-$ type, 2.5 l), eluting with a 0.02 to 0.04M aqueous saline solution for fractionation. Active fractions were combined (5 l), and then concentrated. The concentrate (0.4 l) was subjected to a chromatography on crystalline cellulose (Asahi Chemical Industry Co., Ltd., Japan), eluting with a solvent system of acetonitrile:water (9:1 to 4:1) for fractionation. The fractions exhibiting a single peak with HPLC were combined and concentrated to obtain white powdery TAN-950A monosodium salt (2.59 g).

EXAMPLE 3

Each 40 ml of a medium (pH 7) composed of 2.0% glucose, 3.0% soluble starch, 1.0% corn steep liquor, 1.0% soybean meal, 0.5% peptone, 0.3% sodium chloride and 0.5% calcium carbonate in ten 200 ml-Erlenmeyer flasks was sterilized and inoculated with a loopful of Streptomyces hygroscopicus A-300 (FERM P-1312) grown on a slant culture medium, which was incubated on a rotary shaker (200 rpm) at 28° C. for 48 hours. The obtained culture broth was mixed to give a seed culture broth.

Each 40 ml of a medium (pH 7) containing 5% glycerin, 3.5% de-fatted cotton meal flour and 0.7% precipitated calcium carbonate in 200 ml-Erlernmeyer flasks was sterilized and then cooled.

Two ml of the seed culture broth was used to inoculate the medium in each flask and incubated on a rotary shaker (200 rpm) at 28° C. for 5 days. The obtained culture broth was filtered to give a filtrate (total 4.3 l).

The filtrate was adjusted to pH 3, to which was added ethyl acetate (2 l), and the mixture was stirred for 30 minutes, followed by removal of the ethyl acetate layer. The aqueous layer thus obtained was washed with ethyl acetate (1.5 l) to give 4.2 l of aqueous layer. The aqueous layer was subjected to a column chromatography on Amberlite IR-120 (H$^+$ type, 1 l). The active component was eluted with a 2% aqueous ammonia, and the eluate (5 l) was concentrated. The concentrate was subjected to a column chromatography on Diaion SP-207 (0.3 l) and eluted with water. The antibiotic-active fraction (350 ml) thus eluted was subjected to a column chromatography on QAE-Sephadex (Cl$^-$ type, 100 ml), eluting with a 0.02 to 0.03M aqueous saline solution for fractionation. Active fractions were combined (100 ml), subjected to a column chromatography on crystalline cellulose (70 ml), eluted with a solvent system of acetonitrile-water (85:15-70:30) for fractionation. The fractions containing only TAN-950A with HPLC were combined, concentrated and lyophilized to obtain white powdery TAN-950A monosodium salt (180 mg).

Using Streptomyces hygroscopicus subsp. hygroscopicus IFO 14012, the cultibation was carried out for 4 days in the same manner above-mentioned.

The obtained culture broth (2.8 l) was purified with the same manner above-mentioned to give TAN-950A (sodium salt, 302 mg).

EXAMPLE 4

In 30 ml of 2% sodium hydrogencarbonate solution was dissolved 517 mg of TAN-950A (monosodium salt), then 350 μl of benzoyl chloride was added and stirred for an hour at room temperature. To the reaction solution was added 300 μl of benzoyl chloride and stirred for 3 hours at room temperature while keeping the pH of the solution at 8.0 to 8.5. The obtained reaction solution was washed with ethyl acetate and adjusted to the pH 3.0 with 2N-HCl then washed with ether.

To the resulting aqueous layer was added sodium chloride, which was extracted with 50 ml of ethyl acetate.

After dehydrating using sodium sulfate, the extract was concentrated until dry. The concentrate was treated with ether to obtain white powdery N-benzoyl TAN-950A (460 mg). The powder (100 mg) was treated with methanol-ether to obtain N-benzoyl TAN-950A (70 mg) as crystals.

Melting point: 147°–148.5° C. (decomp.).

Specific rotation: $[\alpha]_D^{22}$ −28.1° (C=0.50 in methanol).

UV spectrum: in methanol λmax ($E_{cm}^{1\%}$) 226 nm (515), 257 nm (410).

IR spectrum (KBr): 3080, 1745, 1650, 1580, 1540 (cm$^{-1}$).

'H-NMR spectrum (DMSO-d6): 12.66 (1H, br.), 8.71 (1H, d, J=7.8 Hz), 8.32 (1H, s), 7.85 (2H, m), 7.50 (3H, m), 4.52 (1H, ddd, J=5.2, 7.8, 9.3 Hz), 2.76 (1H, dd, J=5.2, 14.8 Hz), 2.67 (1H, dd, J=9.3, 14.8 Hz).

FD-MS: m/z 277 (M+H)$^+$.

Elementary analysis ($C_{13}H_{12}N_2O_5$): Calculated: C, 56.52, H, 4.38, N, 10.14. Found: C, 56.50, H, 4.47, N, 10.02.

$^{13}$C-NMR spectrum (DMSO-d6): 172.66 (s), 171.71 (s) 166.25, (s), 151.94 (d), 133.77 (s), 131.33 (d), 128.20 (d), 127.22 (d), 93.36 (s), 52.21 (d), 23.64 (t).

What is claimed is:

1. Antibiotic TAN-950A or a salt thereof, whereof the monosodium salt has the following physico-chemical properties:

(1) Appearance: White solid
   (2) Molecular formula: $C_6H_7N_2O_4Na$
   (3) Ultraviolet (UV) absorption spectrum: in water λmax 253±3 nm ($E_{1\ cm}^{1\%}$=380±50)
   (4) Infrared (IR) absorption spectrum: in KBr Main absorption wavenumbers (cm$^{-1}$) 3430, 1640, 1500, 1410, 1350, 1180, 1070, 930, 870, 810, 750, 610, 530
   (5) $^1$H-nuclear magnetic resonance (NMR) spectrum: 400 MHz, in deuterium oxide The following signals are observed ($\delta_{ppm}$ J$_{(Hz)}$) 2.70 (1H, dd, J=7.3, 15.6), 2.80 (1H, dd, J=4.4, 15.6), 3.86 (1H, dd, J=4.4, 7.3), 7.98 (1H, s)
   (6) $^{13}$C-NMR spectrum: 100 MHz, in deuterium oxide The following signals are observed ($\delta_{ppm}$) 180.6 (s), 177.1 (s), 158.5 (s), 82.9 (s), 58.5 (d), 26.5 (t) and having this structural formula:

2. An antifungal composition useful for treating fungal infections, which contains an effective amount of antibiotic TAN-950having the structural formula or a non-toxic salt thereof, and a pharmaceutically acceptable carrier.

* * * * *